United States Patent [19]

Wright, III

[11] 4,015,607
[45] Apr. 5, 1977

[54] EUSTACHIAN TUBE PROSTHESIS AND METHOD FOR ITS IMPLANTION

[76] Inventor: J. William Wright, III, 7763 Spring Mill Rd., Indianapolis, Ind. 46260

[22] Filed: Jan. 23, 1976

[21] Appl. No.: 651,723

[52] U.S. Cl. .................................. 128/350 R; 3/1
[51] Int. Cl.² .................. A61M 27/00; A61F 11/00
[58] Field of Search ........... 3/1; 128/350 R, 350 V, 128/348, DIG. 20

[56] References Cited

UNITED STATES PATENTS

| | | | |
|---|---|---|---|
| 1,642,819 | 9/1927 | Long | 128/350 R |
| 3,783,454 | 1/1974 | Sausse et al. | 3/1 |
| 3,881,199 | 5/1975 | Treace | 128/350 R X |

OTHER PUBLICATIONS

"Permanent Middle Ear Aeration" by H. Silverstein, Archives of Otolaryngology, vol. 91, Apr. 1970, pp. 313–318.

Primary Examiner—Ronald L. Frinks
Attorney, Agent, or Firm—Woodard, Weikart, Emhardt & Naughton

[57] ABSTRACT

A eustachian tube prosthesis comprising a flanged tube which is positioned in the eustachian tube passageway. The flange is located below the anterior annulus of the middle ear cavity. One end of the tube lies within the middle ear cavity and the other end lies within the eustachian tube passageway. The prosthesis is implanted by lifting the tympanic membrane and inserting the tube past the membrane and into position within the eustachian tube passageway.

11 Claims, 4 Drawing Figures

EUSTACHIAN TUBE PROSTHESIS AND METHOD FOR ITS IMPLANTION

BACKGROUND OF THE INVENTION

1. Field of the Invention

The present invention relates to a device for ventilating and draining the middle ear cavity and, more particularly, to a permanent prosthetic for maintaining patency of the eustachian tube passageway.

2. Description of the Prior Art

The eustachian tube passageway extends from the pharyngeal orifice to its tympanic orifice in the middle ear cavity. The tube consists of an anteromedial cartilaginous two-thirds and a posterolateral bony one-third. The bony portion is also referred to as the protympanum to emphasize that the bony tube is essentially an extension of the tympanic cavity. The length of the tube passageway varies from 31-38 mm, with the protympanum being about 13-14 mm in length. The end portions of the lumen are funnel shaped with the narrow, connecting isthmus measuring about 1 mm wide and 2 mm high.

Functions which have been attributed to the eustachian tube passageway include ventilation and drainage of the middle ear cavity and protection of the cavity from pathology, primarily infection, ascending from the nasal pharynx. Ventilation of the middle ear cavity is important among other reasons to maintain equilibrium with external air pressure across the tympanic membrane. Air enters the middle ear cavity when the passageway opens under normal physiological conditions. The passageway thereby permits adjustment of the air pressure in the middle ear cavity for external pressure changes. The passageway operates in a similar fashion when exposed to pressure changes that occur within the head with respiration, sneezing, speech and other similar conditions. Drainage of the middle ear cavity through the eustachian tube passageway may occur to remove fluids produced in the cavity due to, for example, allergies or infections.

Under certain conditions the eustachian tube passageway or lumen will constrict or become totally obstructed. As a result, the performance of the above-described functions will be inhibited or cease. It then becomes desirable to physically induce the performance of these functions. In addition, the absence of these functions may interfere with the treatment of related ear functions. One of the primary causes of tympanoplasty failure, for example, is the inadequate functioning of the eustachian tube passageway.

Various methods have been devised for restoring ventilation and drainage of the middle ear cavity. Drugs and radiotherapy have been used to directly restore patency of the eustachian tube passageway. For cases in which these methods are unsuccessful, various surgical procedures and implants have been employed.

One of the simpler surgical procedures involves the implantation of a transtympanic ventilation tube. U.S. Pat. No. 3,807,409, issued to Paparella et al. on Apr. 30, 1974 discloses a ventilation tube useful for this purpose. The Paparella et al. device and similar structures are inserted by making an incision in the tympanic membrane or eardrum and placing the ventilation tube therein. These devices, however, are susceptible to being spontaneously extruded into the ear canal after a period of time. Further, the devices while in place render the middle ear cavity vulnerable to infection. The mere existence of a tympanic membrane perforation may also result in problems, although the membrane will usually heal uneventfully after removal or extrusion of the ventilation tube. In general, the use of a transtympanic ventilation tube, though simple and effective for short periods of time, is not suited for use as a permanent implant.

A comparable procedure intended as a permanent measure is described in the Archives of Otolaryngology, p. 315, Vol. 91, April, 1970. In an article entitled "Permanent Middle Ear Aeration", written by Herbert Silverstein, there is described a method for inserting a permanent pressure-equalizing tube for the middle ear. The device comprises a flanged silicone rubber tube having a length of 15 mm, an inside diameter of 1.5 mm, and a flange diameter of 2.5 mm. The tube is inserted through a hole which is drilled in the bony external canal and thereby spans from the middle ear cavity to the outer ear. The disclosed procedure thus includes the disadvantages of requiring a hole to be drilled to provide a location of the tube and of exposing the middle ear to infection.

In "Tympanomaxillary Shunt, A New Method of Middle Ear Ventilation", written by Drs. Drettner and Ekball, in the Archives of Otolaryngology, p. 30, Vol. 90, August, 1969, there is disclosed a procedure for providing a permanent communication between the middle ear cavity and the maxillary sinus. The article concedes, however, that the risk of an ascending infection from the maxillary sinus to the middle ear can not be eliminated and that patients with a history of recurrent sinusitis must be considered unsuitable for this operation. In addition, the procedure is extremely complicated, is not suitable for children, and does not provide a conduit which can serve as an effective drain for the middle ear cavity. An alternative procedure is disclosed by Drs. Lapidot and Kapila in "Experimental Construction of a 'New' Eustachian Tube" appearing in the Archives of Otolaryngology, p. 490, Vol. 86, November, 1967. A conduit less than about 2 inches in length is inserted by a somewhat complicated surgical procedure to span from the middle ear to the oral cavity.

One procedure involves the insertion of a plastic tube within a blocked eustachian tube passageway. This procedure is described in "Therapy of the Eustachian Tube" by Zollner in the Archives of Otolaryngology, p. 394, Vol. 78, September, 1963. The tube is maintained in place by a double-bended end which lies in the middle ear cavity and seats around the round window. The presence of the double bend and the location of the opening within the middle ear, however, prevent the device from functioning as a drainage conduit. The article further relates that 20 of 40 tamponades utilizing the device required a mucous membrane implantation and 8 of the devices in those cases were obstructed.

Silicone rubber tubing, such as that marketed by Dow Corning under the trademark Silastic is used for many of the previously-described devices. Silastic tubing is generally acknowledged to be compatible with body tissue and therefore suitable as a prosthetic implant. Silastic material is also used for breast implantations, to drain areas of the brain, and in other surgical applications. Flanged tubes of other materials are also used in surgical procedures.

The primary requirements for a ventilation restoring procedure and prosthesis are that the technique involve minimal technical difficulties and a negligible risk of complications and that the device provide adequate and permanent ventilation and drainage. In addition, the tympanic membrane should remain intact and there should be no increased risk of middle ear infection. Further, the procedure preferably is applicable to children and adults and should not result in permanent discomfort for the patient.

SUMMARY OF THE INVENTION

A eustachian tube prosthesis is disclosed herein which comprises a flexible tube of a material compatible with body tissue and flange means for positioning the tube within a person's eustachian tube passageway such that one end of the tube is located within the middle ear cavity and the other end of the tube is located within the eustachian tube passageway.

It is an object of the present invention to provide a eustachian tube prosthesis which maintains patency of the eustachian tube passageway and which is not easily extruded.

Another object of this invention is to provide a prosthesis which operates as a ventilation and drainage conduit for the middle ear.

A further object of this invention is to provide a means for ventilating and draining the middle ear while leaving the tympanic membrane intact.

Yet another object of this invention is to provide a means for ventilating the middle ear which does not involve a complicated or technically difficult surgical procedure.

A further object of this invention is to provide a ventilating device which does not increase the risk of middle ear infection while in place.

Still another object of this invention is to provide a surgical procedure and implant for maintaining patency of the eustachian tube passageway which may be used with children or adults.

Further objects and advantages of the present invention will become apparent from the figures and description which follow.

DESCRIPTION OF THE PREFERRED EMBODIMENT

Figure 1:
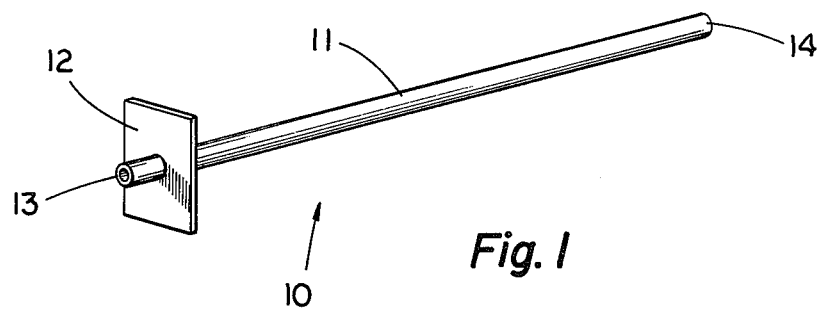
FIG. 1 is a perspective view of the eustachian tube prosthesis of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
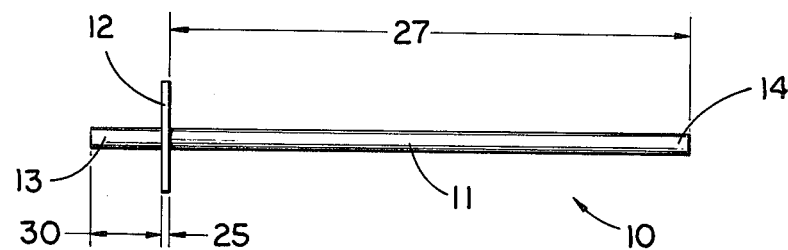
FIG. 2 is a side view of the prosthesis of FIG. 1.
Figure 3:
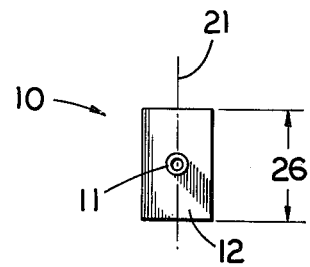
FIG. 3 is an end view of the prosthesis of FIG. 1.

In FIGS. 1–3 there is shown the eustachian tube prosthesis 10 according to the present invention. The prosthesis 10 comprises a tube 11 having a first end 13 and a second end 14. A flange 12 is located near the end 13.

The tube 11 and flange 12 are made of flexible material compatible with body tissue. Several materials are appropriate, but silicone rubber, such as, for example, Silastic has been shown to be well suited and is preferred to materials such as polyethylene. A medical grade silicon adhesive is preferably used to bind the flange to the tubing.

Figure 4:
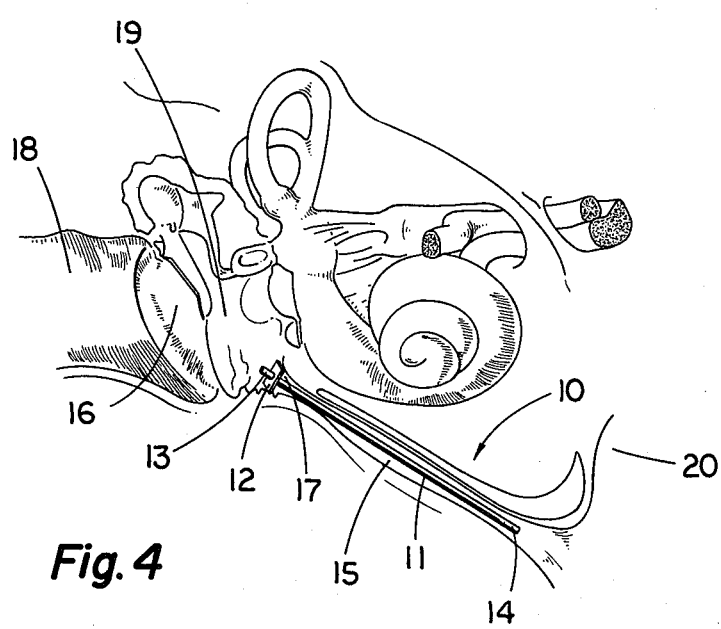
FIG. 4 is a view of the prosthesis of FIG. 1 in position in the middle ear cavity and eustachian tube passageway.

In FIG. 4 there is shown the eustachian tube prosthesis 10 of the present invention in position within the middle ear cavity 10 and the eustachian tube passageway 15. The prosthesis 10 is preferably inserted from the outer ear 18 by a procedure known as a tympanotomy past the tympanic membrane or ear drum 16. The prosthesis may be inserted through an incision in the tympanic membrane 16, but is more preferably inserted by lifting the membrane 16 away from the supporting wall of the ear cavity. It may also be that the patient does not have a tympanic membrane in the subject ear, in which case there is no need for manipulation of the membrane. The end 14 of tube 11 is then threaded into the eustachian tube passageway 18. A wire stylet may be first inserted into the tube to provide sufficient rigidity to the prosthesis to permit insertion into the passageway. The stylet is removed once the tube is in place.

In position, the flange 12 rests upon the funnel-shaped opening of the eustachian tube. The third of the eustachian tube adjacent the middle ear cavity is bone and therefore presents a firm seat for the flange. The flange does not rest on the round window, but rests beneath the anterior annulus 17, which is a bony ledge located near the eustachian tube mouth. The flange preferably has a thickness 25 (FIG. 2) of less than about 4 mm and specifically in one embodiment is a thickness 25 of 0.635 mm to enable it to be positioned below the anterior annulus 17. The flange should also have a greater dimension 26 (FIG. 3) in a plane normal to the tube 11 of at least 4 mm to properly lodge beneath the anterior annulus 17 and to resist extrusion. The flange may have any shape but as shown in FIG. 3 is preferably a rectangle with a length 26 along dimension 21 of at least about 4 mm.

The size of the middle ear cavity and of the eustachian tube passageway will of course vary with each patient. The sizes, however, will generally fall within certain limits. The flange therefore should be located a distance 27 (FIG. 2) not more than about 38 mm and preferably about 32 mm from the end 14 of tube 11, the purpose being to have the tube 11 extend beyond the isthmus of the eustachian tube. Similarly, the flange should be located a distance 30 not more than about 4 mm and preferably about 2 mm from the first end 13 of tube 11. In certain very limited special situations the distance 30 will be lengthened to as much as 15 mm to allow the end 13 to lie in proximity to the round window. These sizes result in proper positioning of the tube 11 upon insertion of the prosthesis within the patient's ear. In addition, the tube 11 preferably has an outside diameter of between about 1.0 mm and about 1.4 mm, preferably 1.2 mm, and an inside diameter of about 0.635 mm. Tubing having an outside diameter of about 0.925 mm and an inside diameter of about 0.508 mm. was found to be inferior in that a greater likelihood of obstruction of the prosthesis resulted.

As shown in FIG. 4, the length of the tube 11 and location of the flange 12 combine to provide a means for properly positioning the ends 13 and 14 of the prosthesis. The flange and the distance from the flange to the first end 13 cooperate to position the first end 13 in the middle ear cavity 19 as desired. The prosthesis thereby operates as a ventilation and drainage conduit for the middle ear cavity and resists blockage. The distance which the tube 11 extends from the flange 12 down the eustachian tube passageway 17 acts to properly position the second end 14. The second end 14 should lie not less than 2 mm from the nasal pharynx end of the eustachian tube passageway. Disadvantages of extending the tube into the nasal cavities 20 include the promotion of tissue growth and tube blockage due to the mucous there present. In addition, further extension of the tube may result in autophony and the ascension of infection from the nasopharynx. The shorter prosthesis extends well beyond the narrow tubal isthmus but does not result in these problems associated with a device which extends into the nasal cavities.

The prosthesis and method of implantation achieve the major requirements for a ventilation and drainage conduit for the middle ear. Thirty eight prostheses of the present invention were inserted in conjunction with a tympanoplasty to improve eustachian tube function. The prosthesis was placed under direct vision at the time of surgery. In some instances the eustachian tube passageway needed to be dilated by use of a no. 50 or 90 polyethylene tube and in exceptional cases a stainless steel wire was used as a stylet during insertion. The eustachian tube passageways were flushed with heparin prior to insertion to minimize the potential of clot formation therein.

Follow-ups of these 38 cases were made for periods from 2 to 13½ months. In thirty of the cases, or about 79 percent, the eustachian tube prosthesis remained patent after the intitial two month healing period. There were no instances of autophony or serious complications in these cases. In addition, the result of a ventilated and drained middle ear cavity was achieved while keeping the ear drum intact and while avoiding an increased risk of middle ear infection. The surgical procedure was found to involve a minimum of technical difficulties and a negligible risk of complications, and the patients experienced no permanent discomfort due to the operation or presence of the prosthesis.

While there have been described above the principles of this invention in connection with specific apparatus, it is to be clearly understood that this description is made only by way of example and not as a limitation in the scope of the invention.

What I claim is:

1. A eustachian tube prosthesis which comprises:
a flexible tube of a material compatible with body tissue, said tube having a first end and a second end; and
flange means mounted on said tube between said first and second ends for positioning said tube within the eustachian tube passageway of a person such that the first end is located within the middle ear cavity and the second end is located within the eustachian tube passageway, said flange means including a flexible flange of a material compatible with body tissue, the length of the tube between said flange and said second end being sufficient to span at least a major portion of the eustachian tube passageway, the flange extending generally radially from the tube, the flange being positioned not more than about 4 mm from the first end of said tube and not more than about 38 mm from the second end of said tube.

2. The prosthesis of claim 1 in which the flange is positioned about 2 mm from the first end of said tube and about 32 mm from the second end of said tube.

3. The prosthesis of claim 2 in which the flange has one dimension in a plane generally normal to the longitudinal axis of said tube of at least about 4 mm.

4. The prosthesis of claim 3 in which said tube has an outside diameter of greater than about 1.0 mm and less than about 1.4 mm.

5. The prosthesis of claim 4 in which said tube and flange comprise silicone rubber.

6. A method for maintaining patency of a eustachian tube passageway which comprises implanting within the eustachian tube passageway a prosthesis including a flexible tube of a material compatible with body tissue, the tube having a first and a second end, the prosthesis further including flange means mounted on the tube between the first and second ends for positioning the tube within the eustachian tube passageway such that the first end is located within the middle ear cavity and the second end is located within the eustachian tube passageway, the first end of said tube being positioned within the middle ear cavity and the second end of said tube being positioned within the eustachian tube passageway.

7. The method of claim 6 in which the second end is positioned not less than 2 mm from the nasal pharynx end of the eustachian tube passageway.

8. The method of claim 7 in which said flange means includes a flexible flange of a material compatible with body tissue, the flange extending generally radially from said tube and being positioned below the anterior annulus of the middle ear cavity.

9. The method of claim 8 in which the flange is positioned about 2 mm from the first end of said tube and about 32 mm from the second end of said tube.

10. The method of claim 6 in which the prosthesis is inserted past the tympanic membrane by lifting the tympanic membrane from the supporting wall of the ear canal.

11. The method of claim 10 in which a stylet is positioned within said tube prior to insertion of said tube into the eustachian tube passageway and is removed when said tube is in place.

* * * * *